United States Patent
Gura et al.

(10) Patent No.: US 8,137,299 B2
(45) Date of Patent: *Mar. 20, 2012

(54) WEARABLE ULTRAFILTRATION DEVICE

(75) Inventors: Victor Gura, Beverly Hills, CA (US);
Edmond Rambod, Los Angeles, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 187 days.

This patent is subject to a terminal disclaimer.

(21) Appl. No.: 12/574,128

(22) Filed: Oct. 6, 2009

(65) Prior Publication Data

US 2010/0022936 A1    Jan. 28, 2010

Related U.S. Application Data

(63) Continuation of application No. 10/251,937, filed on Sep. 19, 2002, now Pat. No. 7,597,677, which is a continuation-in-part of application No. 10/085,349, filed on Nov. 16, 2001, now Pat. No. 6,960,179.

(51) Int. Cl.
*A61M 37/00* (2006.01)
*C02F 1/44* (2006.01)

(52) U.S. Cl. ...... 604/5.04; 604/6.09; 604/6.1; 604/6.11; 210/645; 210/195.2; 210/433.1; 210/416.1; 210/500.21

(58) Field of Classification Search .................. 604/6.09, 604/6.11, 5.01, 5.04, 6.15, 6.16; 210/645–646, 210/600, 634, 644, 195.2, 416.1, 433.1, 321.71, 210/500.21, 258, 259; 422/44
See application file for complete search history.

(56) References Cited

U.S. PATENT DOCUMENTS

| | | | |
|---|---|---|---|
| 3,388,803 | A | 6/1968 | Scott |
| 3,746,175 | A | 7/1973 | Markley |
| 3,884,808 | A | 5/1975 | Scott |
| 3,902,490 | A | 9/1975 | Jacobsen et al. |
| 3,989,622 | A | 11/1976 | Marantz et al. |
| 3,994,799 | A | 11/1976 | Yao et al. |
| 4,000,072 | A | 12/1976 | Sato et al. |
| 4,094,775 | A | 6/1978 | Mueller |
| 4,118,314 | A | 10/1978 | Yoshida |
| 4,209,392 | A | 6/1980 | Wallace |

(Continued)

FOREIGN PATENT DOCUMENTS

CN    1051303    5/1991

(Continued)

OTHER PUBLICATIONS

Ronco, Claudio et al., "The Vicenza Wearable Artificial Kidney for Peritoneal Dialysis (ViWAK PD)," Blood Purification, 2007, pp. 383-388.

(Continued)

*Primary Examiner* — Leslie Deak
(74) *Attorney, Agent, or Firm* — Hamilton, Brook, Smith & Reynolds, P.C.

(57) ABSTRACT

An ultrafiltration device adapted to be worn on a portion of the body of a patient includes a blood inlet tube leading from a first blood vessel, a blood pump, an anticoagulant reservoir for infusing anticoagulants into the blood, a blood filter including a substrate through which the blood is circulated and filtered, a fluid bag for storing the excess fluid and a blood outlet tube leading to a second blood vessel.

14 Claims, 2 Drawing Sheets

U.S. PATENT DOCUMENTS

| | | | |
|---|---|---|---|
| 4,212,738 A | 7/1980 | Henne | |
| 4,247,393 A | 1/1981 | Wallace | |
| 4,267,040 A | 5/1981 | Schal | |
| 4,269,708 A * | 5/1981 | Bonomini et al. | 210/90 |
| 4,326,955 A | 4/1982 | Babb et al. | |
| 4,443,333 A | 4/1984 | Mahurkar | |
| 4,563,170 A | 1/1986 | Aigner | |
| 4,765,907 A | 8/1988 | Scott | |
| 4,806,247 A | 2/1989 | Schoendorfer et al. | |
| 4,828,543 A | 5/1989 | Weiss et al. | |
| 4,897,189 A | 1/1990 | Greenwood et al. | |
| 4,950,395 A | 8/1990 | Richalley | |
| 4,968,422 A | 11/1990 | Runge et al. | |
| 4,997,570 A | 3/1991 | Polaschegg | |
| 5,284,470 A | 2/1994 | Beltz | |
| 5,284,559 A | 2/1994 | Lim et al. | |
| 5,360,445 A | 11/1994 | Goldowdky | |
| 5,391,143 A | 2/1995 | Kensey | |
| 5,405,320 A | 4/1995 | Twardowski et al. | |
| 5,415,532 A | 5/1995 | Loughnane et al. | |
| 5,545,131 A | 8/1996 | Davankov | |
| 5,577,891 A | 11/1996 | Loughnane et al. | |
| 5,725,776 A | 3/1998 | Kenley et al. | |
| 5,846,419 A | 12/1998 | Nederlof | |
| 5,902,336 A | 5/1999 | Mishkin | |
| 5,910,252 A | 6/1999 | Truitt et al. | |
| 5,944,684 A | 8/1999 | Roberts et al. | |
| 5,980,481 A | 11/1999 | Gorsuch | |
| 5,984,891 A | 11/1999 | Keilman et al. | |
| 6,117,100 A | 9/2000 | Powers et al. | |
| 6,117,122 A | 9/2000 | Din et al. | |
| 6,168,578 B1 | 1/2001 | Diamond | |
| 6,196,992 B1 | 3/2001 | Keilman et al. | |
| 6,325,774 B1 | 12/2001 | Bene et al. | |
| 6,332,985 B1 | 12/2001 | Sherman et al. | |
| 6,406,631 B1 | 6/2002 | Collins et al. | |
| 6,491,673 B1 | 12/2002 | Palumbo et al. | |
| 6,561,997 B1 | 5/2003 | Weitzel et al. | |
| 6,610,036 B2 | 8/2003 | Branch et al. | |
| 6,632,192 B2 | 10/2003 | Gorsuch | |
| 6,685,664 B2 | 2/2004 | Levin et al. | |
| 6,706,007 B2 | 3/2004 | Gelfand et al. | |
| 6,758,975 B2 | 7/2004 | Peabody et al. | |
| 6,776,912 B2 | 8/2004 | Baurmeister | |
| 6,796,955 B2 | 9/2004 | O'Mahoney et al. | |
| 6,843,779 B1 | 1/2005 | Andrysiak et al. | |
| 6,890,315 B1 | 5/2005 | Levin et al. | |
| 7,033,498 B2 | 4/2006 | Wong | |
| 7,309,323 B2 | 12/2007 | Gura | |
| 7,351,218 B2 | 4/2008 | Bene | |
| 7,597,677 B2 * | 10/2009 | Gura et al. | 604/5.04 |
| 7,828,761 B2 * | 11/2010 | Gura et al. | 604/5.04 |
| 2002/0112609 A1 | 8/2002 | Wong | |
| 2003/0236482 A1 | 12/2003 | Gorsuch et al. | |
| 2004/0133145 A1 | 7/2004 | Bene | |
| 2006/0241543 A1 | 10/2006 | Gura | |

FOREIGN PATENT DOCUMENTS

| | | |
|---|---|---|
| DE | 20113789 | 5/2002 |
| FR | 2585251 | 1/1987 |
| GB | 2124511 | 2/1984 |

OTHER PUBLICATIONS

Rozga, Jacek et al., "A Novel Plasma Filtration Therapy for Hepatic Failure: Preclinical Studies," Therapeutic Apheresis and Dialysis, 2006, pp. 138-144, Blackwell Publishing Asia Pty. Ltd.

Runge, T. M. et al., "Hemodialysis: evidence of enhance molecular clearance and ultrafiltration volume by using pulsatile flow," The International Journal of Artificial Organs, 1993, pp. 645-652, vol. 16, No. 9., Wichtig Editore, 1993.

Runge, T.M., et al, "Hemodialysis: Evidence of Enhanced Molecular Clearance and Ultrafiltration Volume by Using Pulsatile Flow," Int J Artif Organs, vol. 16, 1993, pp. 645-652.

Sanchez, Cesar et al., Continuous Venovenous Renal Replacement Therapy Using a Conventional Infusion Pump, ASAIO Journal, 2001, pp. 321-324.

Shettigar, "Portable Artifical Kidney With Advantages of Hemodialysis, Hemofiltration, and Hemoperfusion," Artificial Organs, 1982, vol. 1981, No. 5; pp. 645-649.

Shettigar, et al, "A portable hemodialysis/hemofiltration system independent of dialysate and infusion fluid." Artif Organs, vol. 7, No. 2, May 1983, pp. 254-256.

Shinzato, Toru et al., "Newly Developed Economical and Efficient Push/Pull Hemodiafiltration," Effective Hemodiafiltration: New Methods, Contrib Nephrol, 1994, pp. 79-86, vol. 108.

Siaghy, E. M. et al., "Consequences of static and pulsatile pressure on transmembrane exchanges during in vitro microdialysis: implication for studies in cardiac physiology," IFMBE, 1999, pp. 196-201 Med. Biol. Eng. Comput. 37.

Siaghy, E. M., et al, "Consequences of Static and Pulsatile on Transmembrane Exchanges During Vitro Microdialysis: Implication for Studies in Cardiac Physiology," Med Biol Eng Comput, vol. 37, 1999, pp. 196-201.

Suri, R, et al, "Adequacy of Quotidian Hemodialysis," Am J Kidney Dis, vol. 42 Suppl. 1, 2003, pp. S42-S48.

Tsuruta, Kazuma et al, "A Simple Method for Clinical Application of Push/Pull Hemodiafiltration," Effective Hemodiafiltration: New Methods, 1994, pp. 71-78, Contrib Nephrol, vol. 108.

Utsunomiya, T., et al, "Effect of Direct Pulsatile Peritoneal Dialysis on Peritoneal Permeability and Lymphatic Absorption in the Rat," Nippon Jinzo Gakkai Shi, vol. 37, 1995, pp. 24-28.

Vermeulen, Ph. D., Theodore, et al., "Adsorption and Ion Exchange," Perry's Chemical Engineers' Handbook, 1984, Sixth Edition, Section 16, pp. 16-1-16-16.

Welty, J. R., et al, "Chapter 27: Unsteady-state Molecular Diffusion," Fundamentals of Momentum, Heat, and Mass Transfer (2nd ed.), McGraw-Hill, New York, 1984.

Office Action, U.S. Appl. No. 11/933,533, mailed on Jun. 3, 2010.

"Sorbent Dialysis Primer," Organon Teknika Corp , 1991.

Bird, R. B., et al, Transport Phenomena, Wiley, New York, 1976, pp. 126-130, 502-531, 558-563, 624-625, 700-711.

Bosch, T. et al., "Effect of Protein Adsorption on Diffusive and Convective Transport Through Polysulfone Membranes," Contr. Nephrol, 1985, pp. 14-22, vol. 46.

Clark, William R. et al., "Determinants of haemodialyser performance and the potential effect on clinical outcome," Nephrology Dialysis Transplantation, 2001, pp. 56-60, Nephrol Dial Transplant 16 [Suppl 5].

Dellanna, F. et al., "Internal filtration—advantage in haemodialysis?" Nephrol Dial Transplant, 1996, 11 Suppl 2, pp. 83-86, Abstract retrieved from the internet, PMID: 8804002 [PubMed—indexed for MEDLINE].

Ding, L. H., et al, "Dynamic filtration of Blood: A New Concept for Enhancing Plasma Filtration," Int J Artif Organs, vol. 14, 1991, pp. 365-370.

Eloot, S. et al. "In vitro evaluation of the hydraulic permeability of polysulfone dialysers," The International Journal of Artificial Organs, 2002, pp. 210-216, vol. 25, No. 3.

Eloot, S. et al., "Optimisation of solute transport in dialysers using a three-dimensional finite volume model." Comput Methods Biomech Biomed Engin. 2006, pp. 363-370, Abstract retrieved from the internet, PMID: 17145670 [PubMed—indexed for MEDLINE].

Ghezzi, P.M. et al., "Behavior of Clearances and Diffusive Permeability during Hemodialysis with PMMA Dialyzers: Clinical Study," Polymethylmethacrylate. A Flexible Membrane for a Tailored Dialysis, 1998, pp. 53-64, Contrib Nephrol, vol. 125.

Gotch, F. A., "The Current Place of Urea Kinetic Modelling with Respect to Different Dialysis Modalities," Nephrol Dial Transplant, vol. 13 Suppl. 6, 1998, pp. 10-14.

Gotch, F. A., et al, "Effective Diffusion Volume Flow Rates (Qe) for Urea, Creatinine, and Inorganic Phosphorous (Qeu, Qecr, QeiP) During Hemodialysis," Semin Dial, vol. 16, 2003, pp. 474-476.

Gura, V., et al, "Continuous Renal Replacement Therapy for End-Stage Renal Disease: The Wearable Artificial Kidney (WAK)" in Ronco C, Brendolan A, Levin NW (eds), Cardiovascular Disorders in Hemodialysis, Basel, Karger, Contrib Nephrol, vol. 149, pp. 325-333, 2005.

Gura, Victor, et al., "Continuous Renal Replacement Therapy for Congestive Heart Failure: The Wearable Continuous Ultrafiltration System," ASAIO Journal 2006, pp. 59-61.

Henderson, "Continuous Low Flow Hemofiltration With Sorbent Regeneration of Ultrafiltrate," Transactions—American Socitey for Artificial Internal Organs, 1978, vol. 24, pp. 178-184.

Ho, D. W. Y. et al., "Selective Plasma filtration for treatment of fulminant hepatic failure induced by D-galactosamine in a pig model," Gut, 2002, pp. 869-876.

Huang, Zhongping et al., "A New Method to Evaluate the Local Clearance at Different Annular Rings Inside Hemodialyzers," ASIO Journal, 2003, pp. 692-697.

Jaffrin, M. Y. et al., "Rationale of Filtration Enhancement in Membrane Plasmapheresis by Pulsatile Blood Flow," Life Support Systems, 1987, pp. 267-271.

Jaffrin, M. Y., et al, "Rationale of Filtration Enhancement in Membrane Plasmapheresis by Pulsatile Blood Flow," Life Support Systems, vol. 5, 1987, pp. 267-271.

Jaffrin, Michel Y. et al., "Simultaneous Convective and Diffusive Mass Transfers in a Hemodialyser," Transactions of the ASME, Journal of Biomechanical Engineering, May 1990, pp. 212-219, vol. 112.

Kobayashi, E., "A Study of Inorganic Ion Exchangers VII; The Synthesis of gammaNH4ZrH(PO4)2 And Ion-Exchange Properties of gamma-NH4Zr(HPO4)2.2H2O," Bull Chem Soc Jpn, vol. 56, 1983, pp. 3756-3760.

Lande', Arnold J., et al, "In Search of a 24 Hours Per Day Artificial Kidney," Journal of Dialysis, 1(8), 1977, pp. 805-823.

Leypoldt, John K. et al., "Optimization of high-flux, hollow-fiber artificial kidneys," Replacement of Renal Function by Dialysis, 2004, pp. 95-113, 5th Edition, Kluwer Academic Publishers, Great Britain.

Lockridge, R.S. Jr., "The Direction of End-Stage Renal Disease Reimbursement in the United States," Semin Dial, vol. 17, 2004, pp. 125-130.

Lockridge, R.S. Jr., et al, "Is HCFA's Reimbursement Policy Controlling Quality of Care for End-State Renal Disease Patients?" ASAIO J, vol. 47, 2001, pp. 466-468.

Maeda, Kenji et al., "Push/Pull Hemodiafiltration: Technical Aspects and Clinical Effectiveness," Nephron, 1995, Editorial Review, pp. 1-9.

Manns, B.J. et al, "Dialysis Adequacy and Health Related Quality of Life in Hemodialysis Patients," ASAIO J, vol. 48, 2002, pp. 565-569.

Manns, Markus et al, "The acu-men: A New Device for Continuous Renal Replacement Therapy in Acute Renal Failure," Kidney International, vol. 54, 1998, pp. 268-274.

Mapes, D.L. et al, "Health-related Quality of Life as a Predictor of Mortality and Hospitalization: The Dialysis Outcomes and Practice Patterns Study (DOPPS)," Kidney Int., vol. 64, 2003, pp. 339-349.

Marshall, Mark R. et al., "Sustained low-efficiency daily diafiltration (SLEDD-f) for critically ill patients requiring renal replacement therapy: towards an adequate therapy," Nephrology Dialysis Transplantation, 2004, pp. 877-884, Nephrol Dial Transplant 19.

McFarlane, P.A. et al, "The Quality of Life and Cost Utility of Home Nocturnal and Conventional In-center Hemodialysis," Kidney Int., vol. 64, 2003, pp. 1004-1011.

Mineshima, M., et al, "Effects of Internal Filtration on the Solute Removal Efficiency of a Dialyzer." ASAIO J, vol. 46, 2000, pp. 456-460.

Mineshima, Michio et al., "Effects of Internal Filtration on the Solute Removal Efficiency of a Dialyzer," ASAIO Journal, 2000, pp. 456-460.

Mineshima, Michio, "New trends in HDF therapies: Validity of Internal Filtration Enhanced Hemodialysis (IFEHD)," From the Kidney Center, Tokyo Women's Medical University, Japan, date not known, pp. 1-5.

Miwa, M. et al, "Push/Pull Hemodiafiltration: Technical Aspects and Clinical Effectiveness," Artif Organs, vol. 23, 1999, pp. 1123-1128.

Miwa, Toshihiko et al., "Which Kt/V Is the Most Valid for Assessment of Both Long Mild and Short Intensive Hemodialyses?" Nephron, 2002, pp. 827-831.

Mohr, P. E., et al, "The Case for Daily Dialysis: Its Impact on Costs and Quality of Life," Am J Kidney Dis., vol. 37, 2001, pp. 777-789.

Murisasco, A., et al, "A Continuous Hemofiltration System Using Sorbents for Hemofiltrate Regeneration," Clinical Nephrology, 1986, pp. S53-S57, vol. 26, Supp. No. 1.

Murisasco, A., et al, "Continuous Arterio-venous Hemofiltration in a Wearable Device to Treat End-stage Renal Disease," Trans Am Soc Artif Intern Organs, 1986, vol. XXXII, pp. 567-571.

Pascual, Manuel et al., "Is adsorption an important characteristic of dialysis membranes?" Perspectives in Clinical Nephrology, 1996, pp. 309-313, Kidney International, vol. 49.

Patel, S. S., et al, "Psychosocial Variables, Quality of Life, and Religious Beliefs in ESRD Patients Treated with Hemodialysis," Am J Kidney Dis., vol. 40, 2002, pp. 1013-1022.

PCT: Notification of Transmittal of the International Search Report of PCT/US02/30968, dated Nov. 3, 2003, 5 pages.

Roberts, Martin, "Wearable Artificial Kidneys for Continuous Dialysis," ASAIO Journal, 1993, pp. 19-23.

Ronco, C. et al., "Continuous versus intermittent renal replacement therapy in the treatment of acute renal failure," Nephrology Dialysis Transplantation, 1998, pp. 79-85, Nephrol Dial Transplant 13 [Suppl6].

Ronco, C. et al., "The haemodialysis system: basic mechanisms of water and solute transport in extracorporeal renal replacement therapies," Nephrology Dialysis Transplantation, 1998, pp. 3-9, Nephrol Dial Transplant (1998) 13 [Suppl 6].

Ronco, C., "Continuous renal replacement therapies in the treatment of acute renal failure in intensive care patients," Nephrology Dialysis Transplantation, 1994, pp. 191-200, Nephrol Dial Transplant 9 [Suppl 4].

Ronco, C., et al, "Blood and Dialysate Flow Distribution in Hollow-fiber Hemodialyzers Analyzed by Computerized Helical Scanning Technique," J Am Soc Nephrol, vol. 13, 2002, pp. S53-S61.

Ronco, C., et al, "The Hemodialysis System: Basic Mechanisms of Water and Solute Transport in Extracorporeal Renal Replacement Therapies," Nephrol Dial Transplant, vol. 13 Suppl. 6, 1998, pp. 3-9.

Ronco, Claudio et al., "Blood and Dialysate Flow Distributions in Hollow-Fiber Hemodialyzers Analyzed by Computerized Helical Scanning Technique," Journal of the American Society of Nephrology, 2001, pp. S53-S61, J Am Soc Nephrol 13.

Ronco, Claudio et al., "Evolution of synthetic membranes for blood purification: the case of the Polyflux family," Nephrology Dialysis Transplantation, 2003, pp. vii10-vii20, Nephrol Dial Transplant (2003) 18 [Suppl 7].

Ronco, Claudio et al., "Hemodialyzer: From macro design to membrane nanostructure; the case of the FX-class of hemodialyzers," Kidney International, 2002, pp. S126-S142, vol. 61, Supplement 80.

* cited by examiner

WEARABLE ULTRAFILTRATION DEVICE

CROSS-REFERENCE TO RELATED APPLICATIONS

This application is a Continuation of U.S. Pat. No. 7,597,677, issued Oct. 6, 2009, entitled WEARABLE ULTRAFILTRATION DEVICE, which is a Continuation-in-part of U.S. Pat. No. 6,960,179, issued Nov. 1, 2005, entitled WEARABLE CONTINUOUS RENAL REPLACEMENT THERAPY DEVICE, all of which are incorporated herein by reference.

TECHNICAL FIELD

The present invention is directed to ultrafiltration devices, and more particularly to a portable ultrafiltration device that may be continuously worn by a patient.

BACKGROUND

Fluid overload can be caused by many things including metabolic disease, renal failure and, especially, congestive heart failure (CHF), which has become a disease of epidemic proportions all over the globe. CHF is a progressive deterioration of the heart muscle that leads to an inability to pump enough blood to support the vital organs. Deterioration of the heart muscle leads to decreased pumping capacity and increased fluid retention caused by the lack of perfusion pressure of the kidneys due to the failure of the heart to pump enough blood at the proper pressure. Fluid overload can cause leg swelling, shortness of breath and water accumulation in the lungs, impairing the ability to properly breathe.

Removal of excess fluids from the body can be accomplished with diuretics and other drugs that improve the performance of the heart muscle. However, these drugs become gradually ineffective over time and may cause undesirable effects such as kidney failure. In addition, there is a growing body of research supporting the notion that fluid removal by ultrafiltration may be superior to the administration of very large doses of diuretic drugs.

Advantages of ultrafiltration over diuretic drugs include: (1) efficient fluid removal without side effects such as kidney failure and blood pressure drops; (2) prompt relief from shortness of breath and swelling; and (3) improvement regarding certain adverse hormonal effects that are associated with CHF.

Ultrafiltration is performed by pumping blood from a catheter in an artery or a large vein, through a blood filter or a dialyzer, while creating a gradient of pressure through the filter membrane. The pressure gradient forces the passage of fluid out of the blood by convection and the fluid is drained out.

Conventional ultrafiltration devices suffer from several drawbacks. Usually, these devices are cumbersome, heavy and must be hooked to electrical outlets. Since ultrafiltration patients must remain connected to these devices for many hours, their ability to perform normal every day activities is severely limited. In addition, typical ultrafiltration treatments are geared for fast removal of several liters of excess fluid. However, the fluid removal is only temporary and the excess fluid usually reaccumulates in the patient's body after a short period of time. The reaccumulation of fluid is harmful to the patients, as the kidneys are further injured by the progress of CHF and the side effects of the diuretic drugs used to treat the heart.

A further problem with ultrafiltration devices is that repeated reconnection to an ultrafiltration device requires accessing blood flow by puncturing a large blood vessel and forming an arteriovenous shunt. These shunts only last for limited periods of time and are subject to infection, clotting and other complications that result in numerous hospitalizations and repeated surgical interventions. Similar problems also exist when a patient's blood stream is accessed by alternative methods, such as by inserting large catheters into large veins and arteries.

In view of the above disadvantages, there is a substantial need for a portable ultrafiltration device that provides continual, steady and smooth removal of excess fluid from the body.

SUMMARY

The present invention alleviates to a great extent the above-noted and other disadvantages by providing a portable, wearable ultrafiltration device that performs continuous, steady and smooth removal of excess fluid from the body. Importantly, this ultrafiltration device does not require a patient to be hooked up to a large machine for many hours a day, several days per week. Instead, the ultrafiltration device can conveniently be worn on a patient's body for continual use, 24 hours a day, seven days a week, providing steady and smooth removal of excess fluid from the body and preventing the shortness of breath and swelling that are associated with CHF.

One aspect of the present invention involves an ultrafiltration device adapted to be worn on a portion of the body of a patient, including a blood pump and a blood filter for separating excess fluid from the blood.

A further aspect of the present invention involves an ultrafiltration device in the form of a belt adapted to be worn about the waist, shoulder, thigh or other body portion of a patient, wherein the belt includes a pair of end portions which are secured together by a belt fastening means.

Another aspect of the present invention involves an ultrafiltration device adapted to be worn on a portion of the body of a patient includes a blood inlet tube leading from a first blood vessel, a blood pump, an anticoagulant reservoir from which anticoagulants are infused into the blood, a blood filter including a substrate through which the blood is circulated and filtered, a fluid bag for storing the excess fluid and a blood outlet tube leading to a second blood vessel.

These and other features and advantages of the present invention will be appreciated from review of the following detailed description of the invention, along with the accompanying figures in which like reference numerals refer to like parts throughout.

BRIEF DESCRIPTION OF THE DRAWINGS

For a more complete understanding, reference is now made to the following description taken in conjunction with the accompanying Drawings in which.

DETAILED DESCRIPTION

Figure 1:
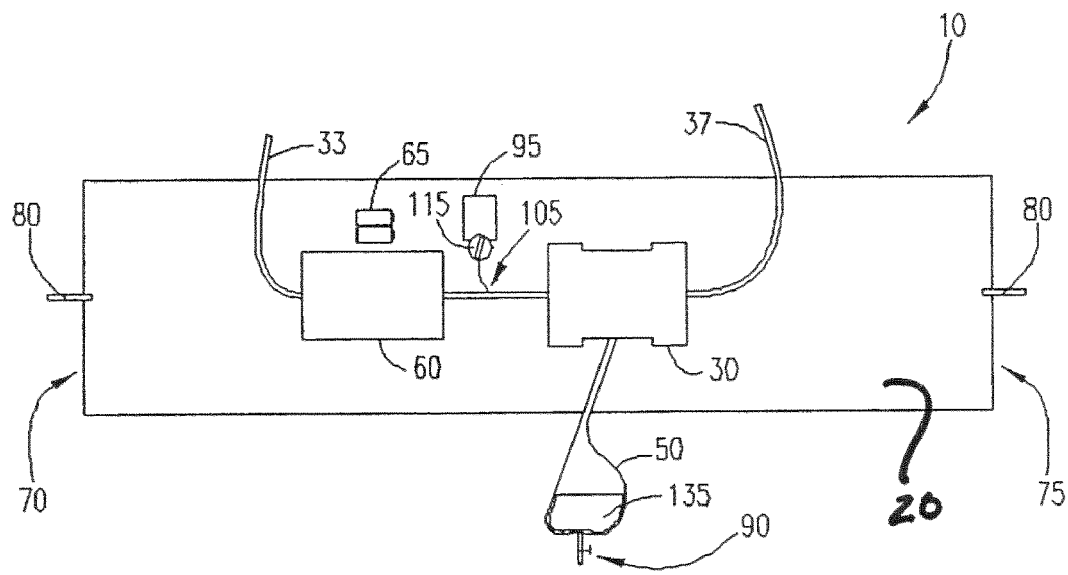
FIG. 1 is a perspective view of an embodiment of an assembly in accordance with the present invention.

Referring now to the drawings, wherein like reference numbers are used herein to designate like elements throughout, the various views and embodiments of a wearable ultrafiltration device are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

Ultrafiltration is a process by which excess fluid in the form of water is removed from the blood, wherein the excess fluid in the blood is moved from one side of a filtering device to another. The filtering device contains many hollow fibers made out of a semipermeable membrane. While blood flows inside of the hollow fibers, water from the blood moves through the membrane wall and is drained off. The purified blood remains inside the hollow fibers and is returned to the body.

Referring to FIG. 1, an ultrafiltration device 10 is designed to extract a targeted volume of fluid from the blood of a patient at a precisely controlled rate. The ability to predictably remove excess fluid from the blood reduces the risk of removing too much fluid too quickly, which can result in low blood pressure and vital organ damage.

The ultrafiltration device 10 comprises a belt 20 adapted to be worn about a portion of the body of the patient. According to some embodiments, the ultrafiltration device 10 is adapted to be worn about the waist of the patient. However, as would be understood to those of ordinary skill in the art, the device 10 may also be worn about other portions of the patient's body, such as over a shoulder or around a thigh. According to some embodiments, the weight of the belt 30 is less than two pounds.

As seen in FIG. 1, the belt 20 includes a pair of end portions 70, 75, which are secured together by a belt fastening means 80 such as a buckle 80, snaps 80, buttons 80 or hook and loop fasteners 80. The belt 20 further includes a blood filter 30 including a blood inlet tube 33 leading from a first blood vessel and a blood outlet tube 37 leading to a second blood vessel in the patient. The belt 20 also includes a blood pump 60, which forces the patient's blood through the filter 30. The pump 60 may be a shuttle pump, piston pump, roller pump, centrifuge pump, piezoelectric pump, or other convention pump. Convention power sources 65 such as batteries 65 can be used to power the blood pump 60.

The blood filter 30 separates excess fluid from the patient's blood. The excess fluid is drained in to an excess fluid bag 50, which is to be periodically emptied via tap 90. The fluid bag 50 can be positioned in the vicinity of a thigh, a leg, an ankle, an arm, or any other suitable body portion of the patient.

The coagulation of the blood circulating through the device 10 is prevented by the constant infusion of anticoagulant, which is infused from an anticoagulant reservoir 95 through a port 105 and into the blood inlet tube 33. In some embodiments, anticoagulant is infused using a battery powered anticoagulant pump 115. The pump 115 may be a shuttle pump, piston pump, roller pump, centrifuge pump, piezoelectric pump, or other convention pump. Typical anticoagulants are infused into the blood 150 include, but are not limited to, heparin, prostacyclin, low molecular weight heparin, hirudin and sodium citrate. According to other embodiments, blood clotting inside the device 10 can be prevented by the oral administration of anticoagulent drugs including, but not limited to, coumadin.

Figure 2:
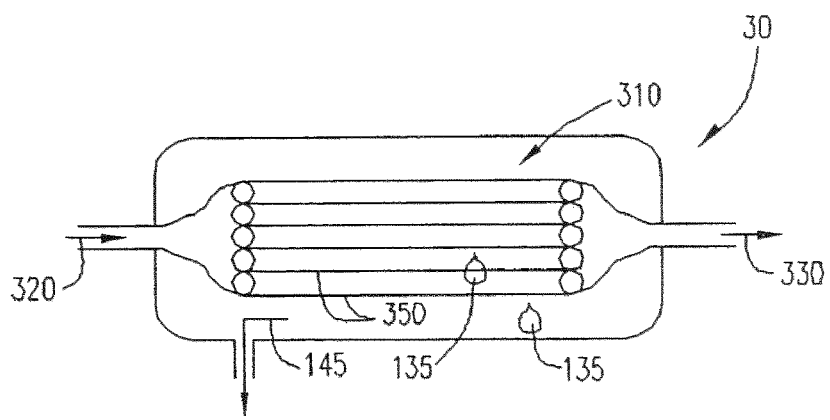
FIG. 2 is a perspective view of an embodiment of an assembly in accordance with the present invention.

Referring to FIG. 2, according to some embodiments, the blood filter 30 is a conventional blood filter 30 comprising a plurality of hollow fibers 310 through which the blood 150 is circulated. The exterior walls 350 of the hollow fibers 310 are semiporous so that excess fluid 135 in the form of water 135 and impurities 135 can be removed from the blood 150. As indicated by arrows 320, 330, excess fluid 135 is drained from the hollow fibers 310, which act as a sieve such that excess fluid 135 passes through, but not blood 150. The excess fluid 135 is drained out of the filter 30 in a direction indicated by arrow 145.

The blood 150 moves through the hollow fibers 310 under pressure from the blood pump 60. This pressure causes the excess fluid 135 in the blood 150 to filter out through the fiber pores, into the other side of the hollow fibers 310, from where the excess fluid 135 is drained out to the fluid bag 50. The magnitude of pressure within the fibers 310 determines the amount of net excess fluid 135 movement removed through exterior walls 350. Small particles within the blood 150 are also removed during this process, but particles larger than the blood filter pore size will be left behind in the blood 150.

Figure 3:
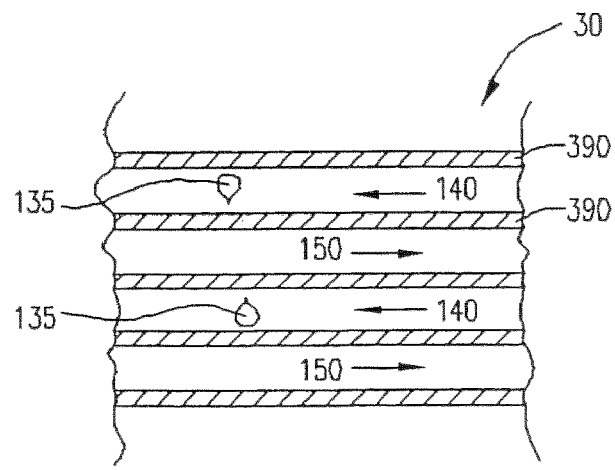
FIG. 3 is a perspective view of an embodiment of an assembly in accordance with the present invention.

Referring to FIG. 3, according to other embodiments, the blood filter 30 is an alternative conventional blood filter 30 comprising a plurality of parallel sheets 390 of semiporous material, wherein air 140 is circulated on one side of the parallel sheets 390 and the blood 150 circulates in the opposite direction on the other side of the parallel sheets 390. The blood filters 30 of these embodiments are conventional and well known in the art. Excess fluid 135 and small particles are removed from the blood 150 through parallel sheets 390 and drained off into excess fluid bag 50.

Figure 4:
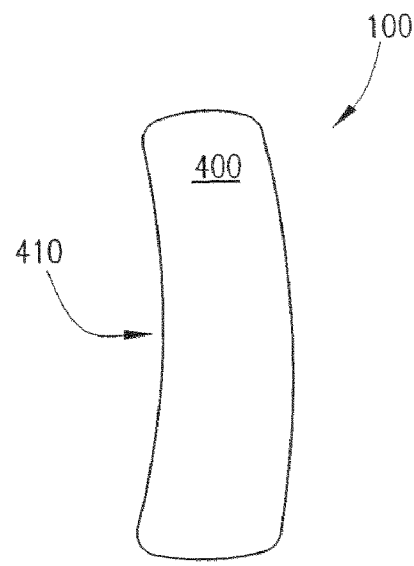
FIG. 4 is a perspective view of an embodiment of an assembly in accordance with the present invention.

Referring to FIG. 4, according to some embodiments, the blood filter 50 has a flexible casing 400 adapted to conform to the body contour of the patient. In addition, the body-side wall 410 of each casing 400 is concave to further correspond to bodily curves of the user. The casing 400 can be made of any suitable material having adequate flexibility for conformance to the portion of the body to which it is applied. Suitable materials include, but are not limited to polyurethane and poly vinyl chloride.

Figure 5:
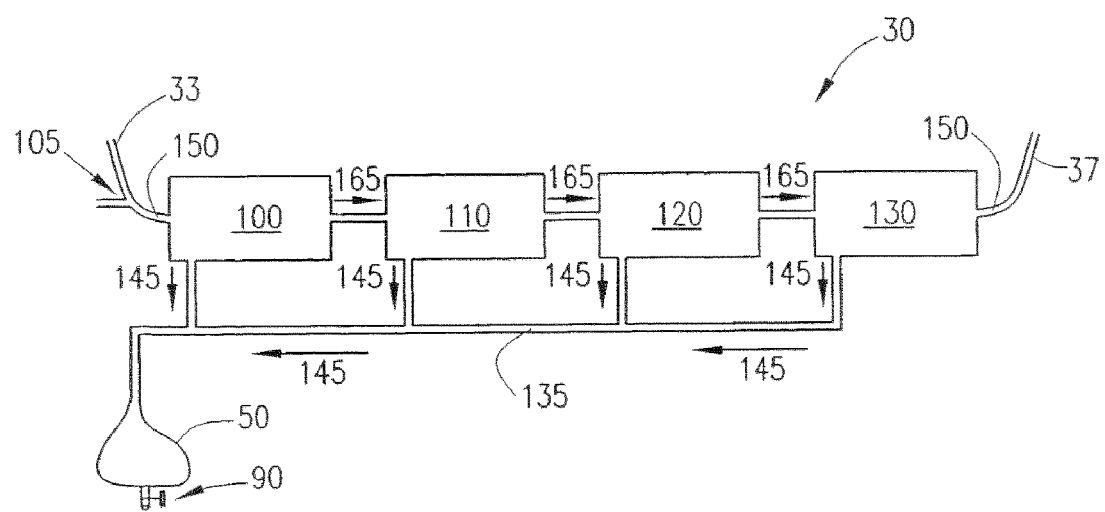
FIG. 5 is a perspective view of an embodiment of an assembly in accordance with the present invention.

Referring to FIG. 5, in an alternative embodiment, the blood filter 30 includes a plurality of miniaturized blood filters 100, 110, 120, 130 that remove impurities from the blood 150 of the patient. The number of filters, 110, 120, 130 in the plurality of filters, 110, 120, 130 may be varied to reflect different ultrafiltration prescriptions. The plurality of blood filters 100, 110, 120, 130 are connected in series, whereby the blood pump 60 forces the patient's blood 150, in a first direction, through the filters 100, 110, 120, 130, as indicated by arrows 165. Excess fluid 135 is drained from the blood filters 100, 110, 120, 130 and into the excess fluid bag 50 as indicated by arrows 145. As would be understood by those of ordinary skill in the art, the filters 100, 110, 120, 130 can also be connected in parallel without departing from the scope of the invention.

Thus, it is seen that a wearable ultrafiltration device is provided. One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

It will be appreciated by those skilled in the art having the benefit of this disclosure that an embodiment of the invention includes a wearable ultrafiltration device that can be completely worn on a portion of a patient's body, can remove excess fluid substantially 24 hours a day, seven days a week and all the while provide steady smooth removal of excess fluid from the patient's body via their blood while the patient is able to perform many normal every day activities because the patient is not limited to a stationary machine plugged into an electrical outlet or limited to lying or sitting in substantial the same position during the excess fluid removal process. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A completely wearable ultrafiltration device comprising:
   a shuttle pump adapted to pump blood from a patient's blood vessel;
   an ultrafiltration filter that receives blood from the shuttle pump, the ultrafiltration filter comprising a plurality of hollow fibers each having semi porous walls such that excess fluid from the blood moves through the semi porous walls at a rate determined by a magnitude of pressure within the plurality of hollow fibers, the magnitude of pressure being created by the shuttle pump, the completely wearable ultrafiltration device constructed and configured to operate and remove excess fluid while in various three-dimensional orientations while being worn on a portion of a patient's body; and
   a fluid bag that receives the removed excess fluid as the excess fluid drains from the ultrafiltration filter.

2. The completely wearable ultrafiltration device of claim 1, further comprising:
   a blood inlet tube that extends from the patient's blood vessel to a shuttle pump input and then from a shuttle pump output to an input of the ultrafiltration filter; and
   an anticoagulant pump connected to the blood inlet tube and adapted to infuse anticoagulant from an anticoagulant reservoir into the blood inlet tube.

3. The completely wearable ultrafiltration device of claim 2, wherein the anticoagulant pump is a piezoelectric pump or a piston pump.

4. The completely wearable ultrafiltration device of claim 1, wherein the completely wearable ultrafiltration device is adapted to operate on a rechargeable battery's power, the rechargeable battery being completely worn on the patient.

5. The completely wearable ultrafiltration device of claim 1, further comprising a blood outlet tube, which carries the patient's blood from the blood filter back to the patient's body.

6. An ultrafiltration device comprising:
   a blood inlet tube adapted to receive blood from a patient's body;
   a shuttle pump that receives blood from the blood inlet tube and pumps the received blood;
   a blood ultrafiltration filter that receives blood forced from the shuttle pump, the blood ultrafiltration filter constructed and configured to filter excess fluid from the blood via pores at a rate determined by a pressure within in the ultrafiltration filter and while in various three-dimensional non-stationary orientations; and
   a fluid bag in fluid connection with the blood ultrafiltration filter, the fluid bag adapted to collect the excess fluid filtered from the blood;
   the ultrafiltration device sized to be completely worn on a portion of the patient's body.

7. The ultrafiltration device of claim 6, further comprising a blood outlet tube to transport filtered blood from a blood ultrafiltration filter output back to the patient's body.

8. The ultrafiltration device of claim 6, further comprising means for infusing anticoagulant into the blood inlet tube.

9. The ultrafiltration device of claim 6, further adapted to comprise a battery for powering the ultrafiltration device.

10. The ultrafiltration device of claim 6, wherein the ultrafiltration device weighs less than 2 pounds.

11. A method of removing ultrafiltrate from a patient's blood comprising:
   obtaining blood from a patient's vessel through a blood inlet tube;
   pumping the blood with a shuttle pump into hollow fibers of a blood filter, the hollow fibers having semiporous walls;
   filtering excess fluid from the blood, without a dialysate fluid, through pores in the semiporous walls;
   directing the filtered excess fluid from the blood filter into a fluid bag while the shuttle pump, the blood filter and the fluid bag are together oriented in various non-stationary three-dimensional orientations.

12. The method of claim 11, wherein the shuttle pump, the blood filter and the fluid bag are all adapted to be worn together on a portion of a patient's body.

13. The method of claim 11, wherein the filtering excess fluid from the blood is done at a rate determined by the pressure of the blood within the hollow fibers.

14. The method of claim 11, further comprising returning blood that exits the blood filter to the patient via a blood outlet tube.

* * * * *